US005542372A

United States Patent [19]
Sun et al.

[11] Patent Number: 5,542,372
[45] Date of Patent: Aug. 6, 1996

[54] PROCESS FOR PURIFICATION OF DMT BY FILM CRYSTALLIZATION

[75] Inventors: Xujiang Sun; Junmin Zhang; Tongshun Wang; Jun Zhang; Hong Su; Hongxia Xia, all of Tianjin, China

[73] Assignee: Tianjin Petro-Chemical Corporation, China

[21] Appl. No.: 337,086

[22] Filed: Nov. 10, 1994

[51] Int. Cl.⁶ .................................................. C30B 29/54
[52] U.S. Cl. .................. 117/68; 117/73; 117/925; 117/927; 23/295 R
[58] Field of Search .................. 117/68, 73, 925, 117/927; 23/295 R; 560/77

[56] References Cited

U.S. PATENT DOCUMENTS

| | | | |
|---|---|---|---|
| 3,485,867 | 12/1969 | Jackson | 260/475 |
| 3,576,842 | 4/1971 | Kimura et al. | 260/475 |
| 3,621,664 | 11/1971 | Saxer | 62/58 |
| 3,686,276 | 8/1972 | Slockett | 260/478 B |
| 4,683,034 | 7/1987 | Bader et al. | 203/43 |
| 5,116,518 | 5/1992 | Bachmann et al. | 210/722 |
| 5,338,882 | 8/1994 | Korte | 562/483 |

*Primary Examiner*—Robert Kunemund
*Attorney, Agent, or Firm*—Ladas & Parry

[57] ABSTRACT

This invention relates to a single crystallization process for purification of dimethyl terephtalate (DMT) by film crystallization, including pumping the raw DMT into a film crystallizer and reducing its temperature to form DMT crystalline on the walls of the crystallizing pipes in the crystallizer, and then heating the crystallizing pipes and collecting the melt at 140°–145° C. The product DMT is thus obtained.

5 Claims, 3 Drawing Sheets

PROCESS FOR PURIFICATION OF DMT BY FILM CRYSTALLIZATION

This invention relates to a process for purification of di-methyl terephthalate (DMT) during its production.

DMT is the raw material for production of polyester. Currently, the principal process for production of DMT is called Witten Process under Nobel Gunpowder Co. German through oxidation of p-xylene (PX) and recycled methyl p-toluate (PTE) with air under the presence of cobaltous/ magnesium acetate catalysis to p-toluic acid (PTS), terephthalic acid (TPA), methyl aldobenzoate (TAE) and other oxidized compounds, followed by esterification of the oxidized products with methanol to form DMT, PTE and other esterification products and then, distillation to have raw DMT separated. But quite a few isomers, such as di-methyl phthalate (DMO), di-methyl isophthalate (DMI) and other impurities, are composed in the raw DMT, which needs further purification.

The purification of raw DMT by Witten process includes the following steps: dissolving DMT into methanol, crystallizing DMT in a crystallizer by reducing temperature and isolating DMT by a centrifuge with most of DMO and DMI remained in methanol solution. The DMT from twice crystallization/isolation still needs final rectification to obtain qualified DMT product with 99.9% in purity. This purification process has the disadvantages of long process scheme, large investment in equipment, high cost of operation, much consumption of energy and the necessity of methanol recovery device owing to the usage of methanol as solvent.

An alternative purification process is called countercurrent stripping process, by which the melting raw DMT produced in oxidation and esterification is led into a countercurrent stripping tower from its top and fresh methanol from its bottom, a DMT suspension is collected at the bottom of the tower, and then, product DMT is obtained after centrifuging and drying. This alternative purification process needs also methanol as solvent.

Up to now, there is no application of film crystallization technology for purification of DMT.

The object of this invention is to provide a purification process for raw DMT, save operation cost, avoid multi-crystallization process in methanol, and obtain the qualified product through only single crystallization of raw DMT in a film crystallizer.

The other object of the invention is to provide a purification process by crystallization of raw DMT with film crystallization technology.

The objects of the invention can be implemented through the process described below.

The purification process of DMT in accordance with this invention includes following steps:

1. pumping the melting raw DMT feed into a film crystallizer, reducing the temperature down to 120°–136° C. to form DMT crystalline film on the walls of the crystallizing pipes of the film crystallizer;

2. heating the crystallizing pipes and collecting melt when the temperature of crystalline film is up to 140°–145° C., thus purified DMT is obtained.

The film crystallizer mentioned above has a vertical parallel pipe structure, with upper portion as a feeding chamber, bottom portion as a discharge chamber and the middle portion as a crystallization section. Crystallizing pipes are evenly arranged inner the shell body of the section. Feeding and discharging chambers are connected through the crystallizing pipes and inlet and outlet openings for heat carrier are located on the shell.

An alternative step 1 is to fill the film crystallizer with raw DMT feed, shut down the supply of feed, closely circulate the raw DMT feed in the film crystallizer while reducing the temperature. DMT crystalline film is thus formed on the walls of the crystallizing pipes in the film crystallizer. The un-crystallized raw DMT feed in step 1 and the melt of 135°–140° C. in step 2 can both be recycled to the feed tank.

The foregoing process can further include a step of incorporation 1–30% by weight, based on the weight of raw DMT feed, organic solvent into the feed for favourite separation of isomers. The boiling point of such solvent should be higher than 135° C.

With the purification process of raw DMT in accordance with this invention, uses of organic solvents with lower boiling points can be reduced or even omitted. Furthermore, DMT product with a purity of 99.99% can be produced through a single operation in one equipment. Thus, the operation procedure is greatly simplified.

The process of the invention is further illustrated with the attached figures, in which,

DETAILED DESCRIPTION OF INVENTION

Figure 1:
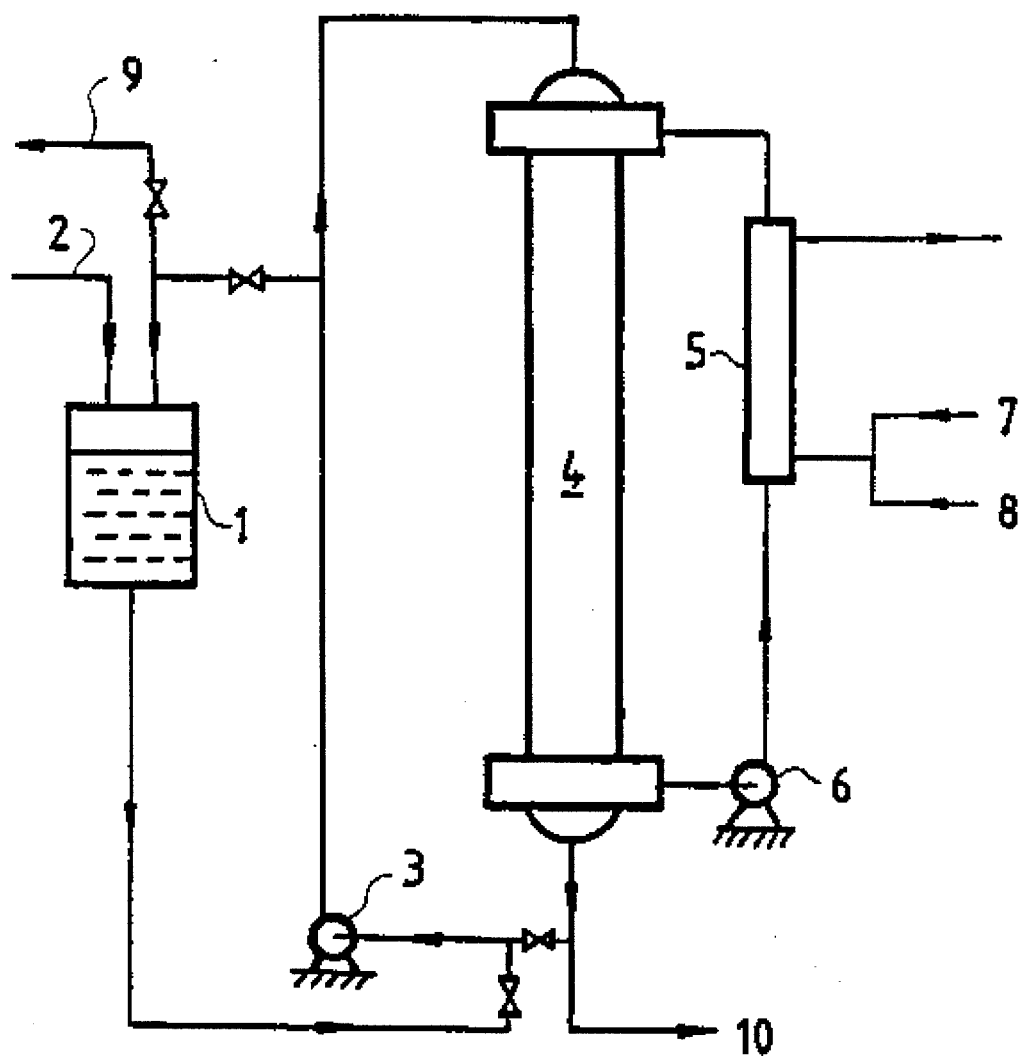
FIG. 1 is a flow scheme of the film crystallization process in accordance with this invention.

This film crystallization process of the invention is a batch process. As shown in FIG. 1, the raw DMT is pumped from the DMT feed tank (1) into the film crystallizer (4) by raw DMT cycling pump (3). Shut down feeding when the crystallizer system is filled with raw DMT. Closely circulate the system while slowly reducing the temperature. When the temperature of raw DMT in the system is reached 120°–136° C., DMT crystalline film is formed on the inner walls of crystallizing pipes (4.3) in the film crystallizer. Stop circulation and drain the un-crystallized raw DMT circulating fluid (9) to a storage tank, partly for re-cycling and partly for recovery treatment. Then, the DMT crystalline film formed is subjected to melting purification, i.e., increasing the temperature of the heat carrier, such as oil or steam, to heat slowly the DMT crystalline film from 120° C. to 145° C. The melt at the temperature of 120°–140° C. is the material rich in DMT isomers, which is pumped back to feed tank (1), and the melt at the temperature of 140°–145° C. is the final product DMT (10).

The film crystallizer mentioned above has a vertical parallel-pipe structure. Two types of film crystallizer with minor different structure, which can be both adopted in accordance with this invention, are shown in FIG. 2 and FIG. 3.

Figure 2:
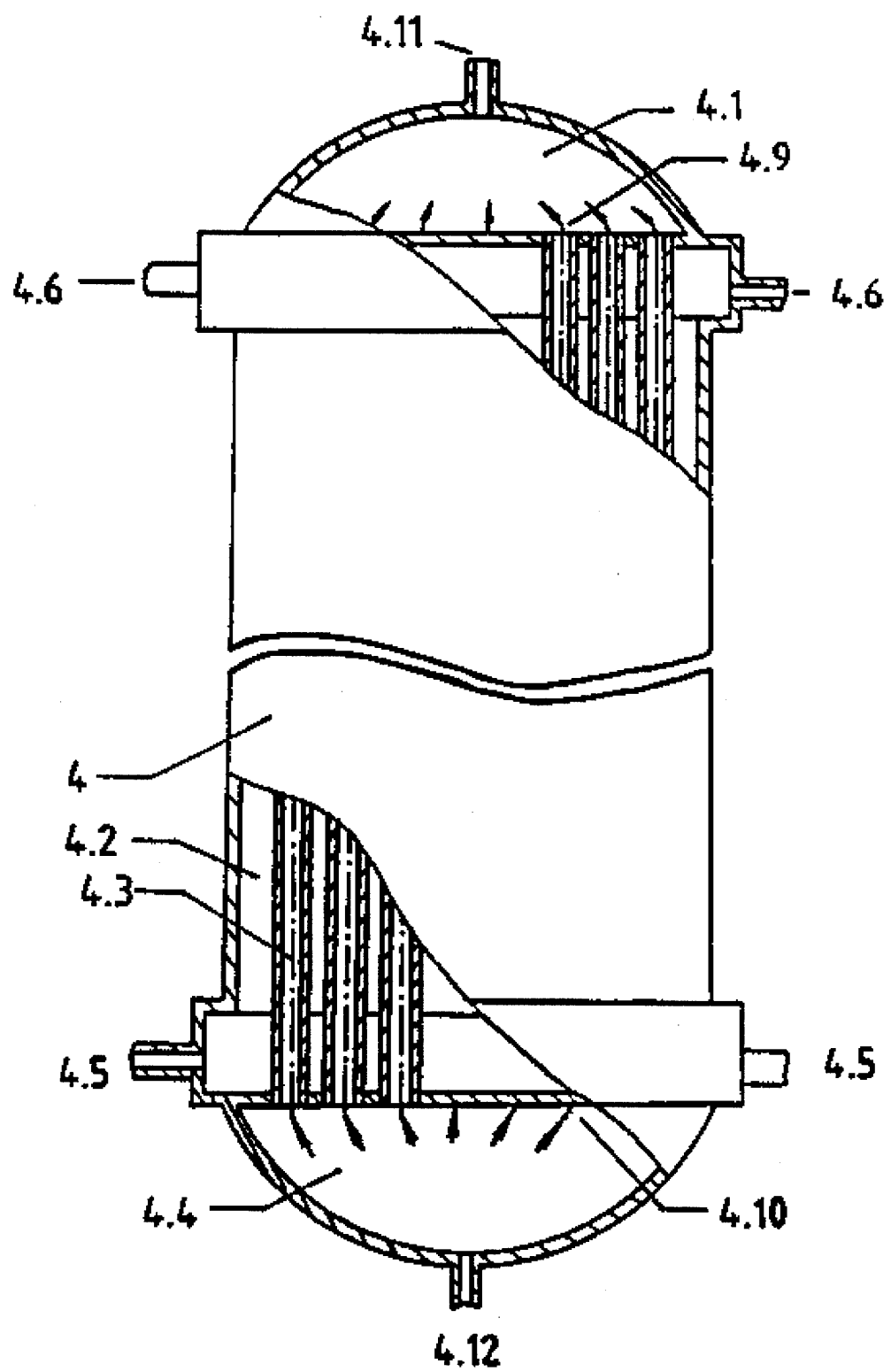
FIG. 2 is the structure of the film crystallizer used in this invention.

As shown in FIG. 2, the upper portion of the film crystallizer is a feeding chamber (4.1) and the lower portion a discharging chamber (4.4). There are feed inlets (4.11) on the feeding chamber (4.1) and an outlet (4.12) on the discharging chamber (4.4). An upper and a lower distribution plates (4.9 and 4.10) in the middle portion of the crystallization section separate the shell passage (4.2) from the feeding and discharging chambers (4.1 and 4.2). In-between the two distribution plates crystallizing pipes (4.3) are evenly arranged according to a certain pattern, for example, triangle. The feeding and discharging chambers are connected through the crystallizing pipes. Around the crystallizing pipes there is a shell body (4), on which are the inlet and outlet openings (4.5 and 4.6) for heat carrier. Heat carrier flows pass the passage (4.2) of the shell body. Inside the crystallizing pipes (4.3) flows the raw DMT fluid. Thus indirect heat exchange takes place between the two fluids. The temperature adjustment of the heat carrier is carried out by a heat exchanger (5), whose heat source comes from steam (7) above 145° C. and the cooling fluid is hot water equal to or below 100° C.

Figure 3:
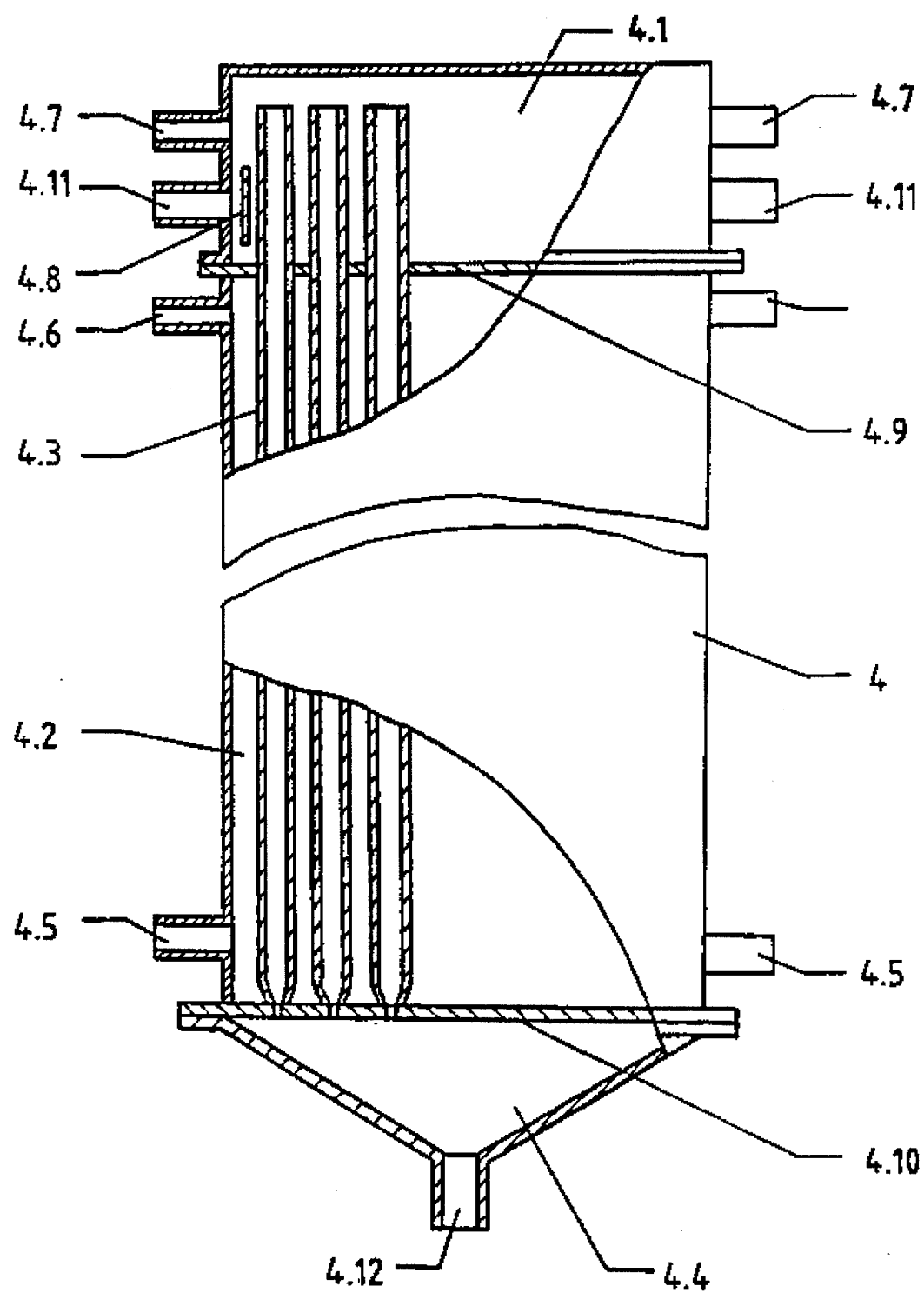
FIG. 3 is the structure of the another crystallizer used in this invention.

Another type of film crystallizer is shown in FIG. 3. What is different from the previous one is that, in addition to feed inlets (4.11) on the feeding chamber (4.1), there are also flow-off (4.7) and baffles (4.8) above the feed inlets (4.6) to ensure the expected flow pattern of the feed in the crystallizing pipe passage.

In accordance with this invention, some small amount of suitable organic solvents can be incorporated into the feed as auxiliaries and can be finally isolated together with impurities. The organic solvents being used should have boiling points higher than 135° C., such as ethylene glycol, p-xylene and mixed xylene. The amount of solvent is or can be used in 1–30%, preferably 1–10%, by weight based on the weight of the feed. In subsequent preparation of polyester, both DMT and ethylene glycol are the feedstokes, therefore, even ethylene glycol is existed in the DMT product purified in accordance with this invention, it is not necessary to remove it out.

The purity of DMT product in accordance with invention is above 99.9% with an acid value equal to or less than 0.01. The operation cost is about 30% lower than that of Witten process. Its flow scheme and equipment is greatly simplified. Accordingly, the process of the invention has better economic benefit.

This invention can be further illustrated in details in following examples, which can never be taken as the limitation of the invention.

EXAMPLE 1

Melt 350 g of feed composed of DMT 82.13%, DMI 11.28%, DMO 3.45%, TAE 0.76%, PTS 0.60% and the others 1.78%, pump it into and recycle it in a crystallizer at the temperature of 140°±2° C. Adjust the temperature of the heat carrier to keep the temperature of the crystallizer at the range of 120°–136° C. for 100 minutes for crystallization. Remove un-crystallized raw DMT and heat the crystallizer to and remain it at 135°–145° C. for purification. The substance obtained from 120°–140° C. is the DMT rich in isomers, which is back to the feed tank for recycling, and the substance above 140° C. is the product with a purity of higher than 99.9%. The purification period id 180 minutes. The amount and composition of resulting individual portions are:

| Product: | 102 g | 99.9% | |
| DMT rich in isomers: | 126 g | 89.48% | (DMI: 6.47%; DMO: 1.86%) |
| DMT recycling fluid: | 112 g | 57.2% | (DMI: 26.5%; DMO: 6.72%) |
| Loss: | 10 g | | |
| Yield in a single pass: | 61.2% | | |

The un-crystallized raw DMT is partially recycled and partially removed from the system for recovery treatment.

EXAMPLE 2

The procedure is the same as described in example 1, except that the feed is 578 g and the composition of the feed is DMT 87.58%, DMI 8.61%, DMO 2.18%, PTS 0.43% and the others 1.21%. The amount and composition of resulting individual portions are:

| Product: | 179 g | 99.99% | |
| DMT rich in isomers: | 202 g | 93.2% | (DMI: 3.21%; DMO: 0.89%) |
| Recycling fluid: | 185 g | 64.8% | (DMI: 18.07%; DMO: 4.38%) |
| Loss: | 21 g | | |
| Yield in a single pass: | 60.5% | | |

EXAMPLE 3

The composition of the feed is the same as that in example 2 and the procedure is the same as described in example 1. After the feed being melted and pumped into the tower, the temperature of the crystallizer is kept at 120°–130° C. for 90 minutes for crystallization. Remove the mother solution and heat the crystallizer to and remain it at 130°–143° C. for 205 minutes for purification. The purity of the product can be higher than 99.99%, which are:

| Product: | 48 g | 99.99% | |
| DMT rich in isomers: | 62 g | 94.2% | (DMI: 3.90%; DMO: 0.22%) |
| Recycling fluid: | 64 g | 61.4% | (DMI: 24.60%; DMO: 6.02%) |
| Loss: | 6 g | | |
| Yield in a single pass: | 55.05% | | |

EXAMPLE 4

Melt 800 g of feed composed of DMT 92.83%, DMI 3.12%, DMO 0/69%, PTS 0.08%, ethylene glycol 2.91% and the other 0.37%, pump it into and recycle it in a crystallizer at the temperature of 140°±5° C. Adjust the temperature of the crystallizer at the range of 133°–139° C. for 100 minutes for crystallization. Remove un-crystallized raw DMT and heat the crystallizer to and remain it at 135°–145° C. for purification. The substance obtained from 133°–140° C. is DMT rich in isomers, which is back to the feed tank for recycling and the substance above 140° C. is the product with a purity of higher than 99.99%. The purification period is 110 minutes. The amount and composition of resulting individual portions are:

| Product: | 288 g | 99.99% | |
| DMT rich in isomers: | 280 g | 90.30% | (DMI: 1.51%; DMO: 0.33% ethylene glycol: 0.76% others: 0.1%) |
| Recycling fluid: | 214 g | 76.73% | (DMI: 9.69%; DMO: 2.15% ethylene glycol: 9.88% others: 1.55%) |
| Loss: | 18 g | | |
| Yield in a single pass: | 63.68% | | |

EXAMPLE 5

Add 50 g xylene into a feed composed of DMT 95.62%, DMI 3.21%, DMO 0.71% and the others 0.46% to turn the composition of the feed to DMT 88.79%, DMI 2.98%, DMO 0.66%, xylene 7.14% and the others 0.43%. Repeat the procedure described in example 4, except that the crystallization temperature is 120°–140° C., the crystallization period is 100 minutes and the purification period is 120 minutes. The DMT content in the product is 99.99%. The amount and composition of resulting individual portions are:

| Product: | 243 g | 99.99% | |
|---|---|---|---|
| DMT rich in isomers: | 240 g | 93.97% | (DMI: 2.23%; DMO: 0.56% xylene: 2.98% others: 0.26%) |
| Recycling fluid: | 197 g | 67.51% | (DMI: 7.87%; DMO: 1.66% xylene: 21.75% others: 1.21%) |
| Loss: | 20 g | | |
| Yield in a single pass: | 64.6% | | |

What we claimed is:

1. A process for purification of DMT including the following steps:

(1) pumping a melting raw DMT feed into a film crystallizer, reducing the temperature down to 120°–136° C. to form DMT crystalline film on the walls of the crystallizing pipes of the film crystallizer, (2) heating the crystallizing pipes and collecting melt when the temperature of crystalline film is up to 140°–145° C. as purified DMT;

and the film crystallizer having a vertical parallel pipe structure, with it upper portion as a feeding chamber, bottom portion as a discharging chamber and the middle portion as a crystallization section; crystallizing pipes being evenly arranged inner the shell body of the section, feeding and discharging chambers being connected through the crystallizing pipes and inlet and outlet openings for heat carrier being located on the shell.

2. A process as described in claim 1, wherein step (1) includes firstly filling the film crystallizer with raw DMT feed, shutting down the supply of feed, closely circulating the raw DMT feed in the film crystallizer while reducing the temperature, and thus forming DMT crystalline film on the walls of the crystallizing pipes in the film crystallizer.

3. A process as described in claim 1 or claim 2, wherein the step (2), the melt between 135°–140° C. is returned back to feed tank.

4. A process as described in claim 1 or 2, wherein a step of incorporating 1–30% by weight, based on the weight of raw DMT feed, organic solvent into the feed is included and the boiling point of such solvent should be higher than 135° C.

5. A process as described in claim 4, wherein the said organic solvents are selected from ethylene glycol, p-xylene and mixed xylene.

* * * * *